United States Patent [19]

Goertz et al.

[11] Patent Number: 4,764,467

[45] Date of Patent: Aug. 16, 1988

[54] PREPARATION OF AN INSOLUBLE BIOCATALYST

[75] Inventors: Hans-Helmut Goertz; Stefan Marcinowski, both of Ludwigshafen; Axel Sanner, Frankenthal, all of Fed. Rep. of Germany

[73] Assignee: BASF Aktiengesellschaft,, Ludwigshafen, Fed. Rep. of Germany

[21] Appl. No.: 45,759

[22] Filed: Apr. 28, 1987

Related U.S. Application Data

[63] Continuation of Ser. No. 504,606, Jun. 15, 1983, abandoned.

[30] Foreign Application Priority Data

Jun. 18, 1982 [DE] Fed. Rep. of Germany ....... 3222912

[51] Int. Cl.$^4$ ................. C12N 11/04; C12N 11/08; C07K 17/08
[52] U.S. Cl. .................................. 435/182; 435/180; 530/817
[58] Field of Search ............... 435/174, 177, 180, 182; 530/817

[56] References Cited

U.S. PATENT DOCUMENTS

| | | | |
|---|---|---|---|
| 3,953,291 | 4/1976 | Chibata et al. | 435/182 |
| 4,138,292 | 2/1979 | Chibata et al. | 435/178 |
| 4,288,552 | 9/1981 | Gestrelius | 435/174 |
| 4,288,562 | 9/1981 | Gestrelius | 435/174 |
| 4,334,027 | 6/1982 | Klein et al. | 435/178 |
| 4,337,313 | 6/1982 | Hershberger et al. | 435/180 |
| 4,440,858 | 4/1984 | Yamaguchi et al. | 435/174 |
| 4,450,233 | 5/1984 | Mimura et al. | 435/178 |

FOREIGN PATENT DOCUMENTS

| | | |
|---|---|---|
| 53764 | of 0000 | European Pat. Off. . |
| 2336829 | of 0000 | Fed. Rep. of Germany . |
| 1479097 | of 0000 | United Kingdom . |
| 1541100 | 4/1976 | United Kingdom . |
| 1517813 | 6/1976 | United Kingdom . |
| 1518746 | 6/1976 | United Kingdom . |

OTHER PUBLICATIONS

Nilsson et al., Biochimica et Biophysica Acta, vol. 268, 1972, pp. 253–256.

*Primary Examiner*—David M. Naff
*Attorney, Agent, or Firm*—Keil & Weinkauf

[57] ABSTRACT

An insoluble biocatalyst is prepared by forming a mixture consisting essentially of the biocatalyst, one or more water-soluble compounds having two or more acrylamide or meth-acrylamido groups and one or more water soluble amines possessing two or more hydrogen atoms bonded to an amine nitrogen, and forming a gel from the mixture. The water-soluble amine is selected from ammonia, lower diamines, lower polyamines, primary monoamines, polyethyleneimine and polyvinylamine. Beads containing the biocatalyst may be formed by suspending the mixture in a water-immiscible solvent to form droplets prior to gelling. The biocatalyst may be an enzyme, cells or cell fragments.

4 Claims, No Drawings

PREPARATION OF AN INSOLUBLE BIOCATALYST

This application is a continuation of application Ser. No. 504,606, filed on June 15, 1983, abandoned.

The present invention relates to a process for the preparation of an insoluble biocatalyst by reacting an amine with a compound possessing two or more acrylamide or methacrylamide groups, in the presence of an enzyme or an enzyme-containing cell substance.

In order to use biocatalysts for carrying out enzymatic reactions, it is desirable in many cases to immobilize them beforehand. The biocatalyst is thus converted to an insoluble form. In an insoluble, finely divided form, it can advantageously be used for a continuous reaction, for example in a column. When the reaction is carried out by a batchwise procedure in which the catalyst is suspended to the reaction medium, the immobilized biocatalyst has the advantage that it can be reused because it can be readily separated off from the reaction solution, for example by filtration or decanting. In many cases, immobilization increases the service life of the biocatalyst so substantially that only then does it become possible to use it economically.

Processes for immobilizing enzymes and cells have been described. In some of these processes, the biocatalyst forms a more or less physical bond to a carrier. For example, the enzyme or the cell can be bonded to the carrier by ionic or adsorptive forces, or can be enclosed in a gel matrix or a membrane. In all these cases, it must be accepted that this type of bonding or enclosure is not permanent, and that the biocatalyst is gradually washed out during use.

In other processes, the biocatalyst is covalently bonded to the carrier. In this case, there are essentially two different procedures. In one of these, it is necessary first to prepare a carrier which either already contains reactive functional groups because of the way in which it was prepared, or which can be subsequently functionalized or activated. The biocatalyst, generally in the form of a solution, is then brought into contact with a reactive carrier of this type, and covalent bonds are formed. The disadvantage in this case is that the capacity of the carrier is determined by the degree of functionalization, and is in general very low. Moreover, in the case of porous or gelatinous carriers, the pore size has to be carefully matched with the biocatalyst to be immobilized. In addition, the shelf life of the functionalized carrier is in general limited.

Another possible method of producing covalently linked insoluble (immobilized) biocatalysts consists in the preparation of a carrier in the presence of the biocatalyst. This can be carried out as follows: the biocatalyst is first functionalized with a suitable reagent and is then used as a reactant in the preparation of the carrier and incorporated into the latter by covalent bonds. The procedure is simpler if the biocatalyst does not need to be functionalized beforehand, but is incorporated by means of its own functional groups, for example amino groups, this incorporation into the carrier taking place during the preparation of the latter. For example, British Pat. Nos. 1,517,813, 1,518,746 and 1,541,100 describe the immobilization of biological material in polyurethane foams, where the reactive polyisocyanate reacts with the biological material on the one hand and builds up the foam on the other. Because of the high reactivity of the isocyanate prepolymer, it is appropriate in this case to pretreat the dry enzyme with this prepolymer; this greatly restricts the usefulness of the process.

U.S. Pat. No. 4,334,027 describes the immobilization of cells or cell fragments in mixtures of epoxides and suitable hardeners. In this case, however, the process is greatly complicated by the use of an inert auxiliary polymer which influences the shaping of the catalyst and is subsequently removed. Moreover, the epoxides used are water-insoluble, and hence the usefulness of the system is in any case restricted.

U.S. Pat. No. 4,288,552 discloses the preparation of immobilized biocatalysts by reacting the biocatalyst with glutaradialdehyde in the presence of a polyamine in aqueous solution, wherein the biocatalyst is incorporated into the network formed from glutaradialdehyde and the polyamine. The disadvantage in this case is the fact that the mechanical properties of the resulting network are unsatisfactory. Another restriction results from the fact that the polyamine must possess a high percentage of primary amino groups since only these, and not secondary amino groups, effect stable crosslinking with glutarodialdehyde.

It is an object of the present invention to provide a very simple process for immobilizing biocatalysts which avoids the disadvantages of the above processes.

We have found that this object is achieved by a process for the preparation of an insoluble biocatalyst from a synthetic carrier and a biologically active substance firmly bonded to the carrier, wherein the following components, in aqueous solution or suspension, are mixed together;

A an enzyme, cells or cell fragments,
B one or more water-soluble compounds possessing 2 or more acrylamide or methacrylamide groups and
C one or more water-soluble aliphatic amines possessing 2 or more hydrogen atoms bonded to the amine nitrogen, with the proviso that the sum of the average number of acrylamide or methacrylamide groups of component B and the average number of hydrogen atoms bonded to the amine nitrogen of component C, in each case per molecule, is greater than 4, and either the gel formed in the course of from one hour to 4 days at above 15° C. is comminuted, or the aqueous mixture is kept in suspension in a water-immiscible solvent until solidification to droplets takes place and the resulting finely divided catalyst is isolated from the solvent. The present invention furthermore relates to a process for the preparation of an organic compound using an isoluble biocatalyst for the heterogeneous enzyme catalysis, wherein the insoluble biocatalyst is prepared as explained above.

Suitable biologically active substances are enzymes or cells, and the latter may be intact or denatured. Disintegrated, digested or homogenized cells or cell fragments may also be employed. In the case of enzymes, either crude preparations or pure enzymes can be used. Preferred enzymes for the novel process are invertase, glucose isomerase, amyloglucosidase and alpha- and beta-amylase. Other suitable enzymes are oxidoreductases, e.g. alcohol dehydrogenase, lactate dehydrogenase, aminoacid oxidase, peroxidase, catalase, glucose oxidase, alcohol oxidase, succinate dehydrogenase, glutamate dehydrogenase, uricase, phenol oxidase, catechol oxidase, monoamino oxidase, lipoxygenase, luciferase, nitrate reductase, nitrite reductase, chloroperoxidase, acetaldehyde dehydrogenase, aldehyde oxygenase, diaphorase, cholesterol oxidase, glutarthio reductase, hydroxysteroid dehydrogenase, xanthine oxidase, dopamine hydroxylase, cytochrome oxidase, diacetyl reductase, superoxide dismutase and limonate dehydrogenase; transferases, e.g. polynucleotide phosphorylase, dextran sucrase, phosphorylase, carbamate kinase, aminotransferase, transaldolase, methyl transferase, pyruvate kinase, carbamyl transferase, phosphofructokinase and dextran synthetase; hydrolases, e.g. lipase, esterase, lactase, lysozyme, aminoacid acylase, penicillin acylase, cellulase, urease, trypsin, chymotrypsin, glutaminase, asparaginase, papaine, ficin, pepsin, leucinamino peptidase, carboxypeptidase A+B, maringinase, bromelain, subtilisin, phospholipase, isoamylase, cephalosporin amidase, hydantoinase, adenosin deaminase, penicillinase, maltase, dextranase, deoxyribonuclease, sulfatase, pullulanase, phosphatase, alpha-galactosidase and beta-glucanase; lyases, e.g. tryptophanase, tyrosine decarboxylase, oxynitrilase, phenylalanine decarboxylase, phenylalanine ammoniumlase, aminoacid decarboxylase, pyruvate decarboxylase, fumarase, enolase, aspartase, aminolevulin dehydratase and carboanhydratase; isomerase; e.g. aminoacid racemase and triosephosphate isomerase; and ligases, e.g. glutathione synthetase.

For the purposes of the invention, a firm bond between the biologically active substance and the carrier is a bond, preferably a covalent bond, such that the biologically active substance is not washed out from the carrier, even over a long period (except, in certain cases, for a certain initial loss of biologically active substance which was only physically bonded).

An insoluble biocatalyst is one which is suitable for heterogeneous catalysis, i.e. one which, because of its insolubility in the reaction medium (which as a rule is aqueous), its particle size and its sufficiently compact nature, can be readily filtered or separated off from the reaction medium in another manner. Cells and cell fragments are not included here because, although they too are insoluble, they are relatively difficult to filter.

When an aqueous solution or suspension of a biologically active substance (component A) is used, the concentration is not critical and may vary within wide limits. Advantageously, the concentration of the solution or suspension obtained is left unchanged.

Examples of suitable water-soluble compounds possessing 2 or more methacrylamide or, preferably, acrylamide groups (component B) are N,N'-methylenebisacrylamide, N,N'-ethylenebisacrylamide and N,N'-diacryloylpiperazine as well as the corresponding methacryl compounds. The mechanical strength of the resulting gel can be improved if compounds or mixtures of compounds possessing (on average) more than 2, preferably as many as 6, reactive double bonds are employed. Such compounds can be obtained, for example, by reacting a bisacrylamide of the above type, in aqueous solution, with less than an equimolar amount of ammonia or one or more water-soluble amines possessing more than 2 hydrogen atoms bonded to the amine nitrogen. The molar ratio employed is such that there is more than 0.5, preferably from 0.7 to 1, mole of bisacrylamide per amine NH group. The resulting adducts also frequently possess improved water solubility, particularly if one or more of the amines used possess hydrophilic groups, e.g. ethanolamine. The water solubility of component B should be not less than 3, preferably not less than 10, % by weight at room temperature.

Suitable water-soluble amines possessing 2 or more hydrogen atoms bonded to the amine nitrogen (component C) are ammonia, lower diamines, e.g. ethylenediamine, propylenediamine and tetramethylenediamine, and lower polyamines, e.g. diethylenetriomine and triethylenetetramine. Provided that component B possesses more than 2 acrylamide or methacrylamide groups, crosslinking also occurs when primary monoamines, e.g. ethanolamine, methylamine or ethylamine, or secondary diamines, e.g. N,N'-dimethylethylenediamine, ase used. It is sufficient if the sum of the number of acrylamide or methacrylamide groups per molecule of component B and the number of NH groups per molecule of component C is more than 4, i.e. not less than about 4.1, advantageously 4.5 or 5, or preferably even higher. Very particularly preferred amino compounds are polymeric compounds, such as straight-chain or branched polyethyleneimine, or polyvinylamine. These amines substantially improve the mechanical stability of the immobilized biocatalyst.

The immobilized biocatalyst is prepared by mixing the 3 components A, B and C. The two last-mentioned components are advantageously employed as aqueous solutions, the concentrations being preferably from 20 to 50% by weight. The molar ratio of the acrylamide or methacrylamide groups of component B to the amine hydrogen atoms of component C is preferably from 1:0.5 to 1:20. The biologically active substance (component A) is advantageously used as a solution or suspension but may furthermore be employed in the form of a powder. Preferably, this substance is first mixed with a solution of component B, a certain time (from 1 minute to 2 hours) is allowed to elapse and a solution of component C is then added. However, a different sequence is also possible, depending on the particular case.

Component C can be added in neutralized, partially neutralized or non-neutralized form, depending essentially on the stability of the pH of the biologically active substance. If the amino compound is employed in a non-neutralized form, the pH of the reaction mixture is in general very high (e.g. from 9 to 11). Under these conditions, gel formation is relatively rapid. However, such a high pH has a denaturing action on many enzymes, and it is therefore advisable to neutralize component C. A substantial advantage of the process described here is that gel formation occurs even at a relatively low pH, e.g. from 5 to 6, even if at a slower rate.

Provided that it is permitted by the thermostabilitty of the biologically active substance used, gel formation can be carried out at elevated temperatures, e.g. 50° C., thereby accelerating it substantially. Temperatures below room temperature are of no advantage. Gel formation can take from one hour to 4 days, preferably from 2 to 8 hours. For economic reasons, longer times are not very useful.

The gel can be comminuted by a conventional method, e.g. by passing it through a sieve, cutting it or extruding it. It can be dried, if appropriate freeze-dried, either before or after the comminuting process. Particle diameters of from 0.1 to 5 mm have proved advantageous.

In order to convert the mixture to a finely divided solid product at the outset, the mixture can be suspended in a stirred inert water-immiscible solvent, if appropriate with the aid of a conventional suspending agent. The mixture then forms solid beads, whose size can be varied within the above range (from 0.1 to 5 mm diameter) in a conventional manner by suitable choice of vessel, stirrer and stirring velocity. Particularly suitable water-immiscible solvents are aliphatic, cycloaliphatic and aromatic hydrocarbons, e.g. hexane, cyclohexane and toluene, and chlorohydrocarbons, e.g. 1,1,1-trichloroethane. In order to effect better suspension, it is advantageous to add suspending agents to the aqueous phase. Suitable substances for this purpose are those used in reverse suspension polymerization, e.g. sorbitan esters. After solidification, the catalyst is filtered off and washed thoroughly with water or an aqueous buffer solution. Washing it beforehand for a short time with a water-soluble organic solvent, e.g. acetone or an alcohol, can be advantageous but is not necessary in every case.

In immobilizing a biocatalyst, it is critical that the biological activity is very substantially retrained during the immobilization process, and that the action of the resulting catalyst remains stable during storage and in particular under the conditions required for the intended reaction (principally temperature and pH). The mechanical strength is also of some importance. In the case of a large number of biocatalysts, none of the conventional immobilization methods gives a satisfactory result. Many of the methods are expensive, others are restricted to a narrow pH range, and in the majority of cases the residual activity after immobilization is low or short-lived. The process according to the invention is superior to the conventional ones, frequently in more than one respect.

EXAMPLE 1

25 mg of $\beta$-fructosidase were dissolved in 5 ml of 0.05 M sodium acetate solution at pH 5.3. To this stirred solution were added, in succession, 5 ml of a 20% strength solution of an adduct of 4,7,10-trioxatridecane-1,13-diamine with N,N'-methylenebisacrylamide (molar ratio 1:4) and 5 ml of a 25% strength aqueous solution of polyethyleneimine (MW 30,000; brought to pH 6.0 with hydrochloric acid). This mixture was left at room temperature for two days. The resulting solid gel was forced through a sieve to give particles of less than 500 $\mu$m size, and the product was washed with 0.05 M sodium acetate solution at pH 5.3. 2.5 g of the immobilized product (corresponding to 4.2 mg of the enzyme employed) were incubated for 30 minutes at 30° C. with 50 ml of a 30% strength sucrose solution. The conversion, determined polarimetrically, was 30%. This corresponds to a residual activity of 70%, based on a corresponding amount of free enzyme.

EXAMPLE 2

5 g of dry yeast were suspended in 50 ml of 0.9% strength sodium chloride solution, and the suspension was left for 1 hour, after which it was centrifuged and the supernatant liquid was decanted. The moist yeast was mixed with 25 g of a 40% strength aqueous solution of an adduct of N,N'-methylenebisacrylamide, ethanolamine and ethylenediamine (molar ratio 8:4:1) and 25 g of a 25% strength aqueous solution of polyethyleneimine (MW 30,000; brought to pH 6.0 with hydrochloric acid), and the mixture was left at room temperature for 3 days. The resulting solid gel was comminuted to give particles of <500 $\mu$m size. 16.2 g of this gel (corresponding to 1.25 g of dry yeast) were introduced into a column, and a 35% strength sucrose solution which had been brought to pH 5.3 with 0.02 mole/liter of sodium acetate was passed over the gel at 30° C. at a rate of 20 ml/hour. The conversion, determined polarimetrically, was 88.5% after 2 days, 87% after 16 days and 84.5% after 28 days.

EXAMPLE 3

1 g of dry yeast was suspended in 10 ml of 0.9% strength sodium chloride solution for 1 hour, after which the suspension was centrifuged and the supernatant liquid decanted. Moist yeast (3.0 g) was mixed with 5 g of a 40% strength aqueous solution of an adduct of N,N'-methylenebisacrylamide, ethanolamine and ethylenediamine (molar ratio 8:4:1) and 5 g of a 25% strength aqueous solution of polyethyleneimine (MW 30,000; brought to pH 6.0 with hydrochloric acid). The resulting mixture was suspended in 100 ml of cyclohexane (suspending agent: 100 mg of protective colloid A as described in German Laid-Open Application DOS No. 2,634,486), and the suspension was stirred for 3 days at room temperature. It was then filtered, and the soild catalyst was washed with 1 liter of 0.05 M sodium acetate buffer at pH 5.3.

To determine the invertase activity, 2.6 g of the catalyst (corresponding to 0.2 g of dry yeast) were shaken in 50 ml of a 30% strength sucrose solution (pH 5.3) for 90 minutes at 30° C. The conversion, determined polarimetrically, was 15%. This corresponds to a residual invertase activity of 50%.

EXAMPLE 4

4 mg of $\alpha$-amylase (130 units/mg) were dissolved in 2 g of a 20% strength aqueous solution of an adduct of 4,7,10-trioxatridecane-1,13-diamine with N,N'-methylenebisacrylamide (molar ratio 1:4), and the resulting solution was mixed with 2 g of a 25% strength solution of polyethyleneimine (MW 30,000; brought to pH 6.0 with hydrochloric acid). The mixture was left to stand for 3 days at room temperature, after which the resulting gel was forced through a sieve of 500 $\mu$m mesh size and the product washed with 100 ml of 0.05 M aqueous sodium acetate buffer solution at pH 6.0. To determine the activity, 1 g of the gel was shaken in 50 ml of a solution of 5 g of Zulkowsky starch (Merck) in 0.016 M sodium acetate buffer solution (pH 6.0) for 30 minutes at 30° C. The resulting oligosaccharides were determined with 3,5-dinitrosalicylic acid, in accordance with P. Berenfeld (Methods in Enzymology, Vol. I, 149, Academic Press, 1955). The activity of the gel was 57.2 units/g, and the yield of immobilized product was 44%.

EXAMPLE 5

8 mg of $\beta$-amylase (28 units/mg) were immobilized to give 4 g of gel by a method similar to that described in Example 4. The comminuted gel was washed with 100 ml of 0.05 M aqueous sodium acetate buffer solution at pH 4.6. To determine the activity, 1 g of gel was shaken in 50 ml of a solution of 5 g of Zulkowsky starch (Merck) in 0.05 M sodium acetate buffer solution (pH 4.8). The maltose formed was determined with 3,5-dinitrosalicylic acid by the method due to P. Berenfeld (loc. cit.). The activity of the gel was 38.6 units/g, and the yield of immobilized product was 69%.

EXAMPLE 6

Amyloglucosidase was immobilized by a method similar to that described in Example 5. The yield of immobilized product was 38%.

We claim:
1. A process for the preparation of an insoluble biocatalyst which consists essentially of:

(1) mixing together the following components in aqueous solution or suspension:
   a. biologically active enzyme, cells or cell fragments,
   b. one or more water-soluble compounds possessing two or more acrylamide or meth-acrylamide groups, and
   c. one or more water-soluble amines possessing two or more hydrogen atoms bonded to an amine nitrogen, said amines being selected from the group comsisting of ammonia, primary aliphatic monoamines, lower aliphatic polyamines, straight chain and branched chain polyethyleneimines and polyvinylamine with the provision that the sum of the average number of acrylamide or methacrylamide groups of component B and the average number of hydrogen atoms bonded to the amine nitrogen of component C, in each case per molecule, is greater than 4,
(2) maintaining the mixture of a, b and c at a temperature of from 15 C to the highest temperature at which the biologically active enzyme, cells or cell fragments remains thermally stable, until a gel is formed over a period of from one hour to four days, and
(3) comminuting the gel.

2. The process of claim 1, wherein component c is polyethyleneimine.

3. A process for the preparation of an insoluble biocatalyst which consists essentially of:

(1) mixing together the following components in aqueous solution or suspension;
   a. biologically active enzyme, cells or cell fragments,
   b. one or more water-soluble compounds possessing two or more acrylamide or meth-acrylamide groups, and
   c. one or more water-soluble amines possessing two or more hydrogen atoms bonded to an amine nitrogen, said amines being selected from the group consisting of ammonia, primary aliphatic monoamines, lower aliphatic polyamines, straight chain and branched chain polyethyleneimines and polyvinylamine with the proviso that the sum of the average number of acrylamide or methacrylamide groups of component B and the average number of hydrogen atoms bonded to the amine nitrogen of component C, in each case per molecule, is greater than 4,
(2) forming a suspension of said mixed components in a water-immiscible solvent,
(3) maintaining said suspension at a temperature of from 15 C to the highest temperature at which the biologically active enzyme, cells or cell fragments remain thermally stable, over a period of from one hour to four days until soldification of the mixture of a, b and c into droplets takes place, and
(4) isolating the resulting biocatalytic droplets from the solution.

4. The process of claim 3, wherein component c is polyethyleneimine.

* * * * *